(12) United States Patent
McNerney et al.

(10) Patent No.: US 6,287,849 B1
(45) Date of Patent: Sep. 11, 2001

(54) MICROBIOLOGICAL TESTING OF A LIQUID SAMPLE

(75) Inventors: Michael James McNerney, Pretoria (ZA); Eugene Pigott, Montenotte (IE)

(73) Assignee: Amanzi Technologies Limited, Cork (IE)

( * ) Notice: Subject to any disclaimer, the term of this patent is extended or adjusted under 35 U.S.C. 154(b) by 0 days.

(21) Appl. No.: 09/663,699

(22) Filed: Sep. 15, 2000

Related U.S. Application Data (63) Continuation of application No. PCT/IB99/00428, filed on Mar. 16, 1999.

(30) Foreign Application Priority Data

Mar. 19, 1998 (ZA) ........................................................ 98/2353

(51) Int. Cl.[7] ............................... C12M 1/12; C12Q 1/24
(52) U.S. Cl. .................... 435/287.1; 435/30; 435/287.6; 435/287.7; 435/287.9; 435/297.2
(58) Field of Search ..................... 435/30, 31, 32, 435/33, 34, 287.1, 287.4, 287.6, 287.7, 287.9, 297.2, 308.1; 210/406, 416.1; 422/101

(56) References Cited

U.S. PATENT DOCUMENTS

| | | |
|---|---|---|
| 2,879,207 | * 3/1959 | Poitras . |
| 2,923,669 | 2/1960 | Poitras ............................... 195/103.5 |
| 3,275,528 | * 9/1966 | Ainis . |
| 3,843,452 | 10/1974 | Freake et al. ....................... 195/103.5 |
| 3,929,583 | 12/1975 | Sharpe et al. ......................... 195/127 |
| 4,485,171 | 11/1984 | Ikeda et al. .............................. 435/30 |
| 4,777,137 | 10/1988 | Lemonnier ............................ 435/299 |
| 4,829,005 | 5/1989 | Friedman et al. .................... 435/296 |
| 5,308,483 | 5/1994 | Sklar et al. ............................ 210/232 |

FOREIGN PATENT DOCUMENTS

| | | |
|---|---|---|
| 0 122 581 A2 | 10/1984 | (EP) . |
| 59-192084 | * 10/1984 | (JP) . |
| 06113817 | 4/1994 | (JP) . |
| WO 91/18085 | 11/1991 | (WO) . |
| WO 96/37600 | 11/1996 | (WO) . |

* cited by examiner

Primary Examiner—William H. Beisner
(74) Attorney, Agent, or Firm—Kenneth H. Johnson (57) ABSTRACT

A culture monitor (10) for microbiological testing of a liquid sample includes a housing having a liquid inlet (30) and a liquid outlet (32, 34), and a liquid sample filtration means inside the housing between the liquid inlet (30) and the liquid outlet (32, 34). The liquid sample filtration means including a filter medium (16) so that a liquid sample entering the housing through the liquid inlet (30) passes through the filter medium (16), with microorganisms present in the liquid sample being retained on the filter medium (16) and spent liquid or filtrate passing through the filter medium (16). A reservoir (53) is provided in the housing downstream of the liquid sample filtration means relative to the liquid inlet (30), with a volume of a rehydration agent for a dehydrated culture medium being provided in the reservoir (53), or the reservoir (53) being adapted to retain during filtration, as a rehydration agent, a portion of the filtrate.

22 Claims, 4 Drawing Sheets

MICROBIOLOGICAL TESTING OF A LIQUID SAMPLE

This application is a continuation of PCT/IB99/00428 filed Mar. 16, 1999, which claims priority from South African patent application 98/2353 filed Mar. 19, 1998.

This invention relates to microbiological testing of a liquid sample. In particular, it relates to a culture monitor and to a kit for microbiological testing of a liquid sample, and to a method of microbiologically testing a liquid sample.

The Applicant is aware of WO 91/18085 which discloses a device for culturing and identifying microorganisms in a liquid sample. The device includes a dry nutrient which is rehydrated during filtration of the liquid sample. The Applicant is also aware of WO 96/37600 which comprises an absorbent support placed under a membrane filter on which microorganisms are retained during filtration. A liquid nutrient medium is supplied to the microorganisms by absorbing the nutrient medium in the absorbent support. The Applicant is further aware of U.S. Pat. No. 4,777,137 which discloses a device which includes a sealed container holding liquid culture medium which is applied directly to a membrane filter with microorganisms.

According to a first aspect of the invention, there is provided a culture monitor for microbiological testing of a liquid sample, the culture monitor including a housing having a liquid inlet and a liquid outlet;

liquid sample filtration means inside the housing between the liquid inlet and the liquid outlet, the liquid sample filtration means including a filter medium so that a liquid sample entering the housing through the liquid inlet passes through the filter medium, with microorganisms present in the liquid sample being retained on the filter medium and spent liquid or filtrate passing through the filter medium; and a reservoir in the housing downstream of the liquid sample filtration means relative to the liquid inlet, with a volume of a rehydration agent for the dehydrated culture medium being provided in the reservoir or the reservoir being adapted to retain during filtration, as a rehydration agent, a portion of the filtrate, the dehydrated culture medium being located such that it is sealed or separated from the spent liquid or filtrate during filtration at least until immediately after filtration of a liquid sample and such that it can be brought into contact with the rehydration agent, after filtration, to form a rehydrated culture medium for the microorganisms retained on the filter medium.

The housing may be adapted to allow the insertion of a dehydrated culture medium into the housing, between the filtration means and the liquid outlet.

The culture monitor may include a cold water soluble gelling agent in the housing between the filtration means and the liquid outlet such that, the gelling agent can be brought into contact with the rehydration agent and the dehydrated culture medium. Instead, the gelling agent may be supplied separately, being insertable into the culture monitor prior to the culture monitor being used to test a liquid sample.

The liquid outlet of the housing may be configured to allow only an excess portion of the filtrate to drain from the reservoir and to retain during filtration, as the rehydration agent, a portion of the filtrate. Thus, an inlet end of the liquid outlet may be raised above a floor of the reservoir, thereby to retain during filtration, as the rehydration agent, a portion of the filtrate. Typically, in one embodiment of the invention, the reservoir retains a 5–20 mi portion of the filtrate.

The housing may define a chamber, which functions as the reservoir. Typically, the housing is modular, comprising at least two separable sections, each section typically being of a synthetic plastics or polymeric material. The sections may be fitted together in a fluid tight manner, e.g. with an interference fit. It is to be appreciated that, by separating the sections of the housing, the dehydrated culture medium and the gelling agent can be inserted into the housing. Typically, the housing is circular cylindrical in outline in plan view.

The reservoir chamber may be a first chamber, the housing including or defining a second chamber downstream of the first chamber relative to the liquid inlet. The second chamber may be defined by a third section of the housing, which may be separable from the rest of the housing. In the same fashion, more chambers downstream of the second chamber may be defined by the housing.

The outlet may extend through the second chamber. Thus, at least until immediately after the monitor has been used to filter the liquid sample, the first chamber and the second chamber of the monitor may be sealed from each other. The outlet may be a two part outlet, comprising an upper section and a lower section, the two sections being displaceable relative to each other. In one embodiment of the invention, the upper section fits in a fluid tight manner in male-female fashion in the lower section, and is axially displaceable relative to the lower section.

The monitor may include removable closure members for the liquid inlet and the liquid outlet respectively. In one embodiment of the invention, the closure members are interchangeable and are in the form of plugs having elongate plug stems which fit spigot-socket fashion into the liquid inlet and outlet, thereby closing off the inlet and outlet, with one of the plugs having a longer plug stem than the other plug.

The culture monitor may be configured to establish contact between the dry culture medium and the rehydration agent. In one embodiment of the invention, a floor of the first chamber has a zone of weakness surrounding the liquid outlet, and in particular the inlet end of the liquid outlet. Thus, in this embodiment, axial displacement of the upper section of the outlet away from the lower section leads to failure of the zone of weakness and allows the rehydration agent in the reservoir or first chamber to be contacted with the dry culture media in the second chamber. Displacement of the upper section of the outlet may be effected by inserting an object, such as the stem of the long stemmed plug, into the lower section of the outlet and exerting a force or a load on the upper section of the outlet, thereby axially to displace the upper section away from the lower section to effect failure of the zone of weakness.

In another embodiment of the invention, the second chamber and the first chamber are each defined by a housing section, the housing sections being screw-threadedly attached or attachable to each other, with a sealed flow passage being provided between the chambers. The seal of the flow passage may be configured to be pierced or broken when the chambers are advanced towards each other by rotating their housing sections relative to each other, thus establishing flow communication between the two chambers.

The second chamber may include or may be defined by one or more compartments, e.g. 2–8 compartments. The or each compartment may be sealed from the rest of the second chamber, and/or the compartments may be sealed from each other. The compartment(s) may be annular or circular. The or each compartment may be configured to release its contents when so required. Thus, the compartments may hold the rehydration agent, which may be deionised sterilized water; the dehydrated culture medium; the gelling agent; a supplementary growth nutrient; and/or a non-target bacterial growth inhibitor. The compartments may also hold separated constituents of the dehydrated culture media, thus advantageously prolonging the shelf life of the monitor. It is to be appreciated that, if the monitor stores a volume of rehydration agent, then there is no need to retain a portion of the filtrate, and the reservoir or first chamber does not need being adapted to retain during filtration, as the rehydration agent, a portion of the filtrate.

In one embodiment of the invention, a single compartment is provided in the second chamber, the compartment being in the form of an annular channel formed between the floor of the first chamber and a floor of the second chamber with the channel being sealed from the rest of the compartment by complementary annular male and female formations on the floors of the chambers. Release of the contents of the channel is thus effected by displacing the floor of the first chamber and the floor of the second chamber away from each other, thereby to break the seal formed between the male and female formations. In this embodiment, a flow path may exist between the first chamber and the second chamber, e.g. the flow path may be defined by a space between the floor of the first chamber and a wall of the housing.

A dehydrated culture medium may be located or locatable in the second chamber, or, as stated above, in a compartment of the second chamber.

The filtration means may include an absorbent body supporting the filter medium. The absorbent body may be in the form of an absorbent pad of, e.g., a cellulosic material.

The filter medium may be a membrane filter, e.g. a mixed cellulose ester membrane. Typically, the membrane filter has a pore size of 0.45 $\mu$m or 0.22 $\mu$m.

The filtration means may include a support for the absorbent pad and/or the filter medium. The support may be in the form of a perforated disk. Distribution/drainage channels may be provided in a surface of the disk which is in contact with the absorbent pad or the filter medium, as the case may be, with the distribution/drainage channels leading to the perforations or apertures in the disk. Instead, the disk may be made from a porous plastics material or it may be in the form of a fine mesh.

In one embodiment of the invention, the dehydrated culture medium is contained in a slow-release capsule. The capsule may be of a cold water soluble material, e.g. gelatine or a dissolvable vegetable cellulose. Preferably, the material of the capsule should not detrimentally affect the pH or the nutrient value of the rehydrated culture medium. Typically, the capsule dissolves in about 5–20 minutes in water, and dissolution of the capsule is typically accelerated upon incubation of the monitor. The capsule may be located in the first chamber, or in a chamber downstream of the first chamber.

Instead, or in addition to being dissolvable, the dehydrated culture medium may be contained in a fragile or breakable capsule, which may be located or locatable in the housing such that it can be broken or crushed to release its contents. Such a fragile or breakable capsule may be located in the first chamber, and may be broken or crushed to release its contents by displacing the floor of the first chamber towards the support of the filtration means. Instead, such a capsule may be broken by piercing it with, e.g. the long stemmed plug by locating the capsule over the inlet end of the outlet and inserting the stem of the long stemmed plug into the outlet.

Instead of being contained in a capsule, the dehydrated culture medium may be contained in one or more of the chambers of the monitor, in powdered or agglomerated/ granular or compressed form, e.g. in the second chamber as hereinbefore described.

As mentioned before, the monitor may include a gelling agent, e.g. in combination with the dehydrated culture medium, or in one of the compartments or in a capsule, advantageously assisting in contacting the rehydrated culture medium with the filter medium. It is to be appreciated that in such a case, the absorbent body may not be required. Examples of suitable gelling agents are hydroxyethyl cellulose, carboxymethyl cellulose, polyacrylamide, locust bean gum, algin, guar gum and xantham gum.

As will be appreciated, the dehydrated culture medium in the monitor or for use with the monitor is selected based on the microorganisms to be tested for in the liquid sample. For example, for testing for faecal and/or total coliforms in water, an MFC Broth or Membrane Lauryl Sulphate Broth, the former being available in the USA from Millipore Corporation, Bedford, Massachusetts, may be used.

The monitor may include pH indicating means, e.g. a strip of pH indicator paper, inside the housing downstream of the filtration means relative to the liquid inlet. The pH indicating means may be located in the second chamber or in the first chamber.

As mentioned before, the culture monitor may include a non-target bacterial growth inhibitor inside the housing. The non-target bacterial growth inhibitor may be contained in a slow release capsule, similar to the capsule containing the dehydrated culture medium, or in a compartment as hereinbefore described. Such a non-target bacterial growth inhibitor is typically released from the capsule about 3–6 hours after the sample was filtered.

The monitor may further also include a hygroscopic substance inside the housing, to control the humidity inside the monitor.

The culture monitor may include dissolution promoting means to promote the dissolution of the dehydrated culture medium when it is being rehydrated. In one embodiment of the invention, the dissolution promoting means is in the form of at least one displaceable object, e.g. a small steel sphere, which, when the culture monitor is shaken after filtration, assists the dehydrated culture medium to dissolve in the rehydration agent. In another embodiment, the dissolution promoting means is in the form of an agitator rotatably mounted to the raised inlet end of the liquid outlet in such a manner that it can be rotated by inserting a turning handle into the liquid outlet with a cogged end portion of the turning handle connecting in male/female fashion with a cogged receiving formation of the agitator. Thus, in use, the agitator is rotated for assisting mixing and dissolution of the dehydrated culture medium. It is to be appreciated that the cogged receiving formation of the agitator is situated axially above the inlet end of the liquid outlet and that it does not interfere with the flow of filtrate through the liquid outlet.

According to a second aspect of the invention, there is provided a kit for microbiological testing of a liquid sample, the kit including a culture monitor as hereinbefore described; and a sample container for use with the culture monitor.

The sample container may include a hollow body having a liquid outlet at a low elevation, the liquid outlet being connectable to the liquid inlet of the culture monitor. Preferably, the body is graduated for volumetric measurement, and has a volumetric capacity of at least 100 ml. Flow control means, e.g. a stop cock, or a plug, may be provided in the outlet of the sample container.

The kit may include a base which is configured to support the monitor. The base may include a suction or vacuum tube or pipe or conduit which is connectable to the outlet of the monitor. The base may have mounting means, e.g. apertured wings or eyelets, for mounting it on a working surface.

According to a third aspect of the invention, there is provided use of a culture monitor as hereinbefore described, in a method of microbiologically testing a liquid sample.

According to a fourth aspect of the invention, there is provided use of a kit as hereinbefore described, in a method of microbiologically testing a liquid sample.

In use, the liquid sample may be filtered through the culture monitor, the dehydrated culture medium may be rehydrated with the rehydration agent, the gelling agent, if present, may be contacted with the rehydration agent, and the culture monitor may be turned upside down. If required, at least one of the liquid inlet or liquid outlet may be plugged, prior to turning the culture monitor upside down. The microorganisms may then be incubated on the filter medium.

According to a fifth aspect of the invention, there is provided a method of microbiologically testing a liquid sample, the method including filtering a liquid sample through a filter medium to retain microorganisms present in the liquid sample on the filter medium, with a filtrate passing through the filter medium;

As after filtration of the liquid sample, bringing a dehydrated culture medium into contact with a portion of the filtrate to provide a rehydrated culture medium; and contacting the rehydrated culture medium with the microorganisms on the filter medium thereby to culture the microorganisms.

The method may include admixing a gelling agent with the rehydrated culture medium, thereby assisting in contacting the rehydrated culture medium with the microorganisms on the filter medium.

The method may include incubating the microorganisms on the filter medium.

The invention will now be described, by way of example, with reference to the accompanying diagrammatic drawings, in which.

Figure 1:
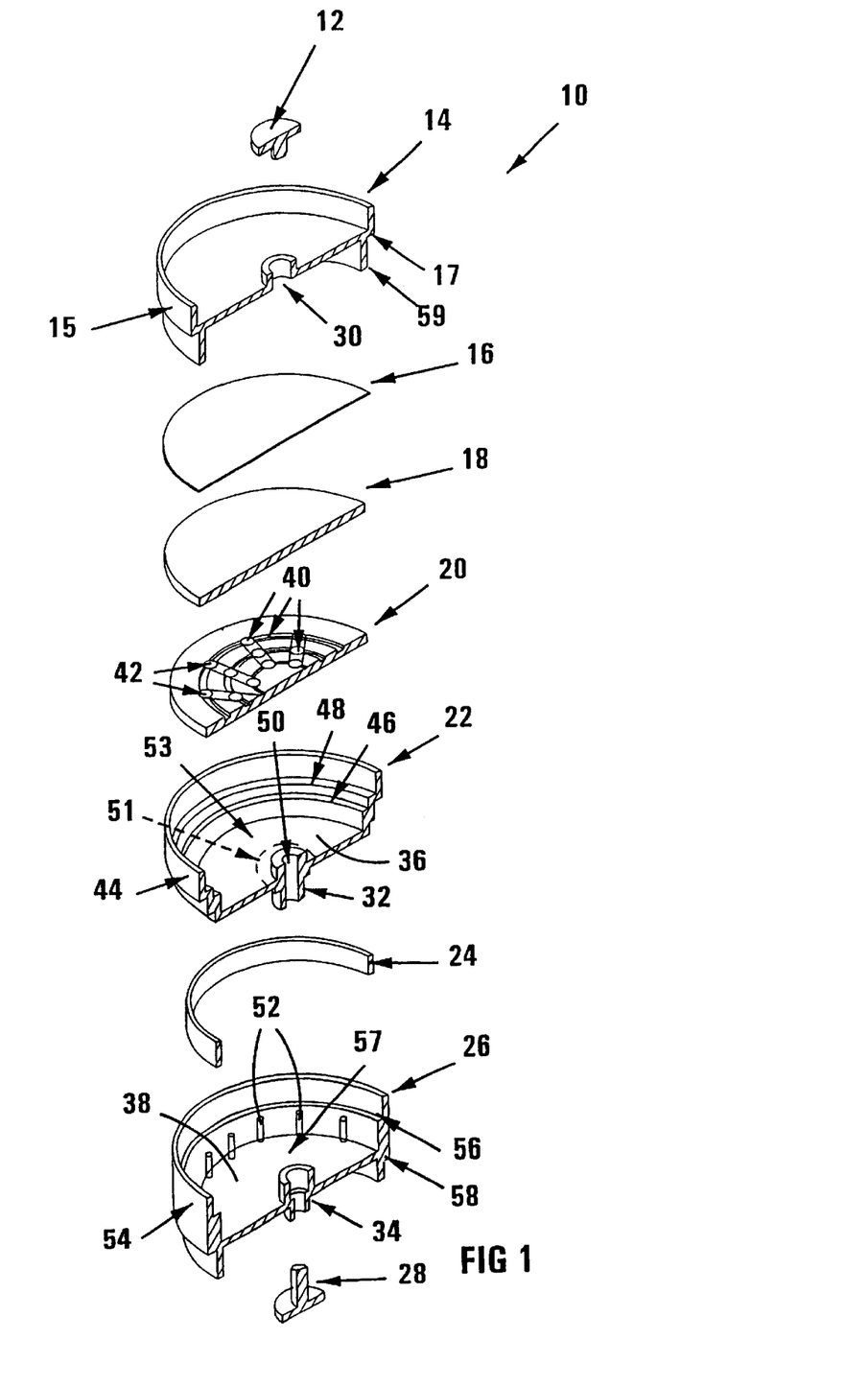
FIG. 1 is an exploded, sectioned three-dimensional view of a culture monitor forming part of a device in accordance with the invention for microbiological testing of a liquid sample.

Referring to FIG. 1 of the drawings, reference numeral 10 generally indicates a culture monitor forming part of a kit in accordance with the invention for microbiological testing of a liquid sample. The monitor 10 includes a short stemmed plug 12, a first housing section 14, filtration means comprising a filter medium 16, an absorbent pad 18 and a support 20, a second housing section 22, a strip of pH indicator paper 24, a third housing section 26 and a long stemmed plug 28. Unless otherwise indicated, all the components of the monitor 10 is of a synthetic plastics or polymeric material.

An inlet 30 is provided in the first housing section 14 and an outlet, comprising an upper outlet section 32 located centrally in a floor 36 of the second housing section 22 and a lower outlet section 34 located centrally in a floor 38 of the third housing section 26 is provided. The stems of the short stemmed plug 12 and the long stemmed plug 28 are dimensioned to fit interchangeably in a fluid-tight manner into the inlet 30 and the lower outlet section 34.

The filter medium 16 comprises a membrane filter with a pore size of 0.45 gm. The absorbent pad 18 consists of a cellulosic material and has the same diameter as the support 20, which has a smaller diameter than the filter medium 16. The support 20 is in the form of a disk having distribution/drainage channels 40 and openings 42 located in the distribution/drainage channels 40, perforating the disk.

The first housing section 14 has a stepped wall 15, defining an overhang 17. The second housing section 22 has a stepped wall 44 defining two ledges or shelves 46, 48 respectively. The upper outlet section 32 has an inlet end 50 which is raised above or is standing proud of the floor 36 of the second housing section 22. A zone or line of weakness 51 in the floor 36 of the second housing section 22 surrounds the inlet end 50. The second housing section 22 and the support 20 defines a reservoir or first chamber 53 between the floor 36 and the support 20.

The third housing section 26 has a plurality of retaining elements 52 spaced equidistantly apart adjacent a periphery of the floor 38 of the third housing section 26. A small gap is provided between the retaining elements 52 and a stepped wall 54 of the third housing section 26. The gap between the retaining elements 52 and the wall 54 is sufficient to receive the strip of pH indicator paper 24 between the retaining elements 52 and the wall 54. The stepped wall 54 defines a ledge or shelf 56 and an overhang 58. The third housing section 26 and the second housing section 22 defines a second chamber 57 between the floor 38 and the floor 36, when assembled. When assembled, the support 20 and absorbent pad 18 rest on the shelf 46 of the second housing section 22 and the filter medium 16 rests on the shelf 48. The absorbent pad 18 and the support 20 are of such thickness that an upper surface of the absorbent pad 18 is flush with the shelf 48. The first housing section 14 fits with an interference fit in a fluid-tight manner in male-female fashion into the second housing section 22, such that the overhang 17 rests on the rim 22. The filter medium 16 is thus sandwiched or clamped between a lower rim 59 of the first housing section 14 and the shelf 48 of the second housing section 22. If desired, the filter medium 16 may be glued to the shelf 48, thus trapping the absorbent pad 18 and the support 20.

The second housing section 22 fits with an interference fit and in a fluid-tight manner in male-female fashion into the third housing section 26. An underside of the shelf 46 of the second housing section 22 rests on the shelf 56 of the third housing section 26 with the floor 36 of the second housing section 22 resting on top of the retaining elements 52.

A dry culture medium in powder form (not shown), such as MFC Broth or Membrane Lauryl Sulphate Broth (when the monitor 10 is intended for coliform testing in water), and, if desired, a gelling agent is contained in the third housing section 26 in the second chamber 57. As will be appreciated, when the monitor 10 is assembled, the dry culture medium in the second chamber 57 is separated and sealed from the reservoir or first chamber 53.

In its assembled form, the monitor 10 is stackable and can be supplied sterilized in packs of multiple units.

Figure 4:
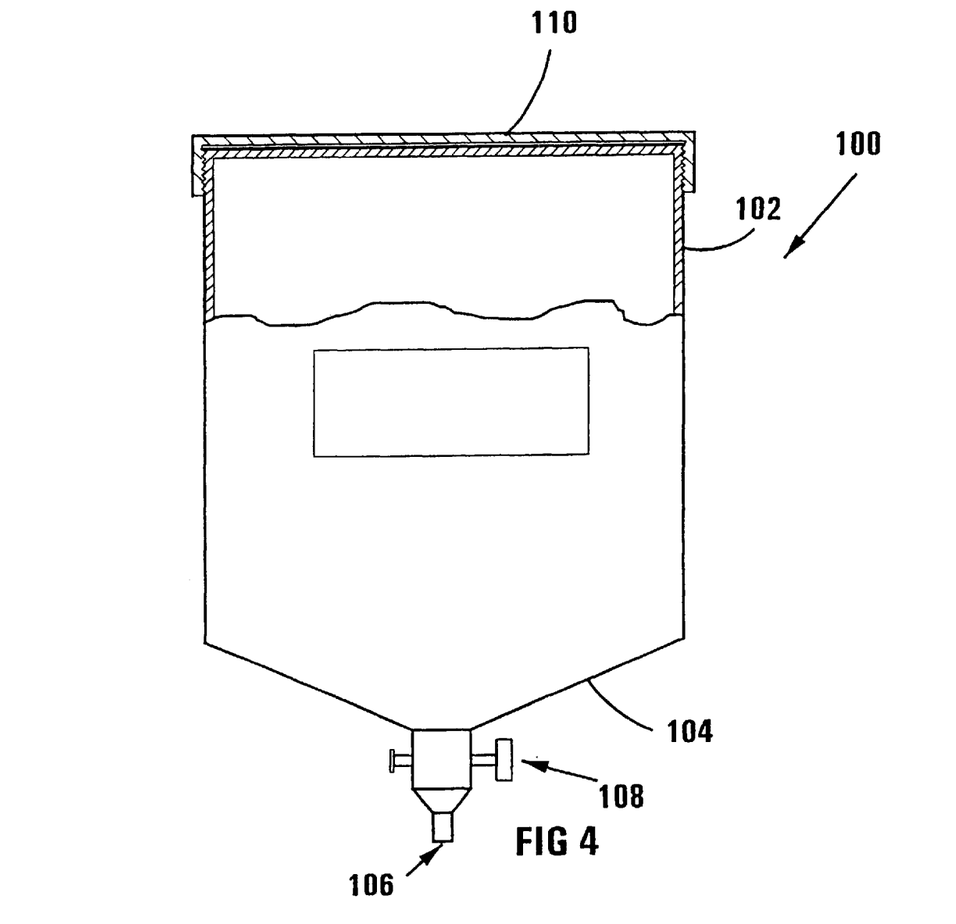
FIG. 4 is a partially sectioned side view of a sample container forming part of a kit in accordance with the invention.

Referring to FIG. 4 of the drawings, reference numeral 100 generally indicates a sample container, forming part of the kit of the invention. The sample container 100 comprises a hollow body 102 with a frusto-conical 10 bottom 104 and an outlet 106. A stop cock 108 is provided in the outlet 106 and a fluid tight screw on closure member 110 is provided for the body 102. The body 102 is graduated to show volumes up to a 100 ml. The sample container 100 may be of an autoclaveable synthetic plastics or polymeric material or of glass, so that the sample container 100 may be sterilised and used repeatedly.

Figure 5:
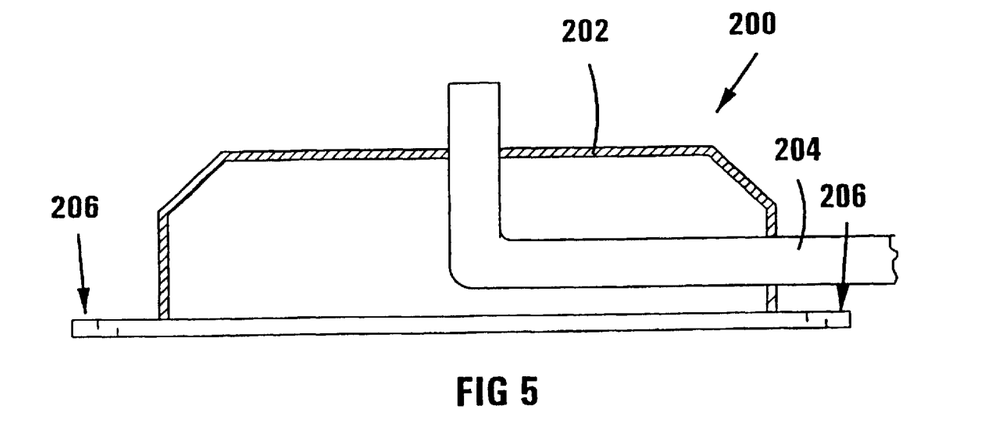
FIG. 5 is a partially sectioned side view of a base forming part of the kit of the invention.

Referring to FIG. 5 of the drawings, reference numeral 200 generally indicates a base which forms part of the kit of the invention. The base 200 is configured to support the third housing section 26. The base 200 includes a support member 202 on which the third housing section 26 can be placed, and a suction or vacuum tube or pipe 204 which is connectable to the lower outlet section 34 of the third housing section 26. Apertured wings or eyelets 206 are provided for mounting the base 200 on a working surface.

In use, a volume of water to be microbiologically tested, for example for faecal coliforms, is collected in the body 102 of the sample container 100. Typically, at least 100 mi is collected in the body 102 as a sample. The stop cock 108 can be used to drain some of the water to obtain a desired sample volume. With the closure member 110 screwed on and the stop cock 108 closed, the liquid sample can be conveyed, if necessary, to a location where the testing is to be performed. The outlet 106 of the sample container 100 is inserted into the inlet 30 of the first housing section 14 after the long stemmed plug 28, which is normally located in the inlet 30, is removed. The short stemmed plug 12, which is normally retained in the lower outlet section 34 of the third housing section 26, is removed and the lower outlet section 34 is connected to the vacuum tube or pipe 204 of the base 200.

The stop cock 108 is opened, the closure member 110 is removed and a vacuum is applied via the vacuum tube or pipe 204, to suck the water sample through the filter medium 16, the absorbent pad 18 and the support 20. Microorganisms present in the water sample are retained on the filter medium 16, with a filtrate passing into the reservoir or first chamber 53. The filtrate fills the reservoir or first chamber 53 until there is enough filtrate to overflow into the upper outlet section 32. The excess filtrate flows down the upper outlet section 32 and the lower outlet section 34 into the vacuum tube or pipe 204, where it is evacuated. Typically, a volume of about 5–20 ml of filtrate is retained in the reservoir or first chamber 53.

It should be appreciated that, although the use of filtrate is perfectly acceptable for normal natural liquids, there may be samples, or there may be procedural requirements, that require the use of distilled deionised water for rehydrating the dehydrated culture medium. If distilled delonised water is required, an aliquot, e.g. 20 to 40 ml of distilled/deionised water, can be used as a post-filtration rinse. The filtrate water in the reservoir or first chamber 53 is thus replaced with sterile distilled water.

Instead of using the sample container 100, the housing section 14 of the culture monitor 10 can be removed and replaced with an open ended cylinder, with volume indication, which fits into the housing section 22, and into which 100 mi of sample can be poured directly.

Once the 100 mi sample has been filtered, the sample container 100 or open ended cylinder, as the case may be, is removed, the housing section 14 is replaced, if necessary, and the short stemmed plug 12 is inserted into the inlet 30. The outlet section 34 is disconnected from the vacuum tube or pipe 204, and the long stemmed plug 28 is inserted into the lower outlet section 34 until its stem is in contact with the upper outlet section 32. The long stemmed plug 28 is pushed even further upwards into the lower outlet section 34, thus causing the zone or line of weakness 51 to yield or break to form an opening in the floor 36 of the second housing section 22. The filtrate retained in the reservoir or first chamber 53 is then contacted with the dry culture medium and, if present, the gelling agent contained in the second chamber 57 thereby to rehydrate the dry culture medium. The pH indicator paper 24 can be used to check the pH of the rehydrated culture medium. The monitor 10 is then inverted so that the rehydrated culture medium saturates the absorbent pad 18, thus providing nutrient to any microorganisms present on the filter medium 16.

It is to be appreciated that, when the culture monitor 10 is inverted, it is desirable to prevent seepage of the rehydrated culture medium through the absorbent pad 18 and the filter medium 16. If both the liquid inlet 30 and the liquid outlet are plugged, a pressure differential can develop across the filter medium 16 either due to thermal air expansion or to gas production by the target microbiological organism. When the gelling agent is included in the culture monitor 10 it may provide the rehydrated culture medium with sufficient viscosity to prevent free movement of the rehydrated culture medium through the filter medium 16 and the culture monitor 10 may thus be inverted without any plugging of the inlet 30 or the outlet. When the gelling agent is not present, the passage of liquid through the filter medium 16 and the prevention of a pressure differential across the filter medium 16 can be ensured by for instance plugging the raised inlet 30 and by ensuring that the inlet end 50 of the upper outlet section 32 is not submerged in the rehydrated culture medium. If a closed system is required, pressure release means should be provided on the housing sections 14 and 26.

The monitor 10 can be placed inside an incubator for a selected period of time to incubate the microorganisms. For faecal coliforms, the microorganisms are incubated for instance at about 44.5° C. Once incubated, the filter medium 16 can be examined for the formation of colonies of the microorganisms.

Figure 6:
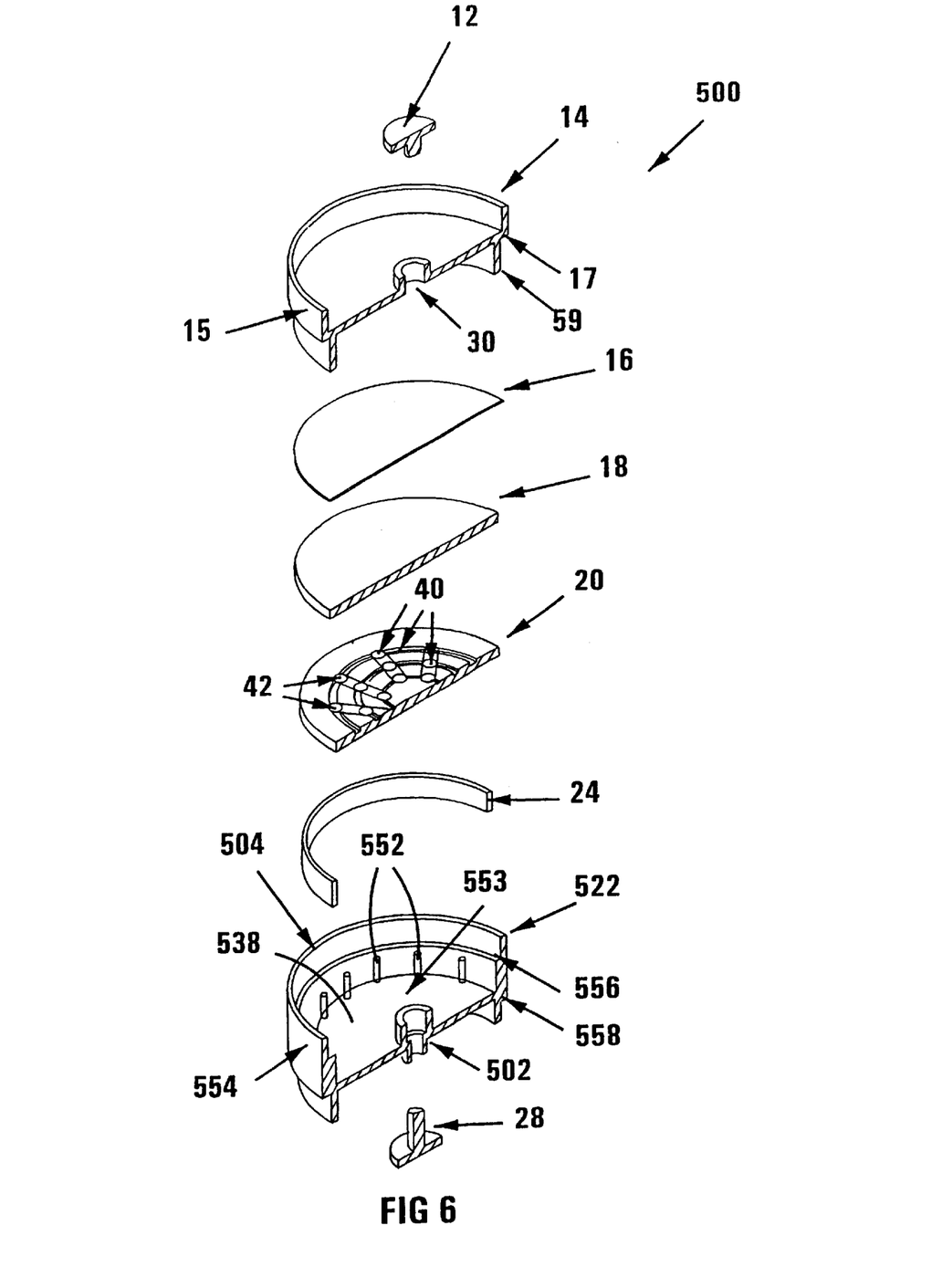
FIG. 6 is an exploded, sectioned three-dimensional view of yet another embodiment of the culture monitor in accordance with the invention.

Referring to FIG. 6 of the drawings, reference numeral 500 generally indicates another embodiment of a culture monitor in accordance, with the invention. Unless otherwise indicated, the same reference numerals used above with reference to FIG. 1, are used to indicate the same or similar parts or features.

Unlike the culture monitor 10, the culture monitor 500 has a first housing section 14 and a second housing section 522, but not a third housing section.

The second housing section 522 has a plurality of retaining elements 552, similar to the retaining elements 52 of the culture monitor 10, spaced equidistantly apart adjacent a periphery of a floor 538 of the second housing section 522. The second housing section 522 has a stepped wall 554 which defines a ledge or shelf 556 and an overhang 558. An outlet 502 is provided in the floor 538. The outlet 502 is similar to the upper outlet section of the culture monitor 10. The second housing section 522 and the support 20 defines a reservoir 553 between the floor 538 and the support 20.

The culture monitor 500 is assembled in similar fashion to the culture monitor 10, with the first housing section 14 fitting with an interference fit in a fluid-tight manner in male-female fashion into the second housing section 522, such that the overhang 17 rests on an upper rim 504 of the second housing section 522. The filter medium 16, absorbent pad 18 and support 20 are thus sandwiched or clamped between the lower rim 59 of the first housing section 14 and the shelf 556 of the second housing section 522. In another embodiment (not shown), the absorbent pad 18 and the support 20 are of the same diameter as the reservoir 553 and are thus seated recessed into the reservoir 553 such that an upper surface of the absorbent pad 18 is flush with the shelf 556. The filter medium 16 is thus sandwiched or clamped between the lower rim 59 of the first housing section 14 and the shelf 556 of the second housing section 522 in the same manner as shown in FIG. 1 of the drawings.

A dry culture medium and, if desired, a gelling agent in a slow release capsule (not shown) is contained in the reservoir 553.

The culture monitor 500 is used in fashion similar to the culture monitor 10. However, unlike the culture monitor 10, it is not necessary to introduce, after filtration, the rehydration agent to the capsule containing the dehydrated culture medium, since the capsule is contained in the reservoir 553, which is filled with the filtrate during filtration. Once the capsule has been dissolved and the rehydration of the dehydrated culture medium has occurred, the culture monitor 500 is inverted so that the rehydrated culture medium saturates the absorbent pad 18, as described above, and the monitor 500 is placed inside an incubator for a selected period of time to incubate the microorganisms.

Figure 2:
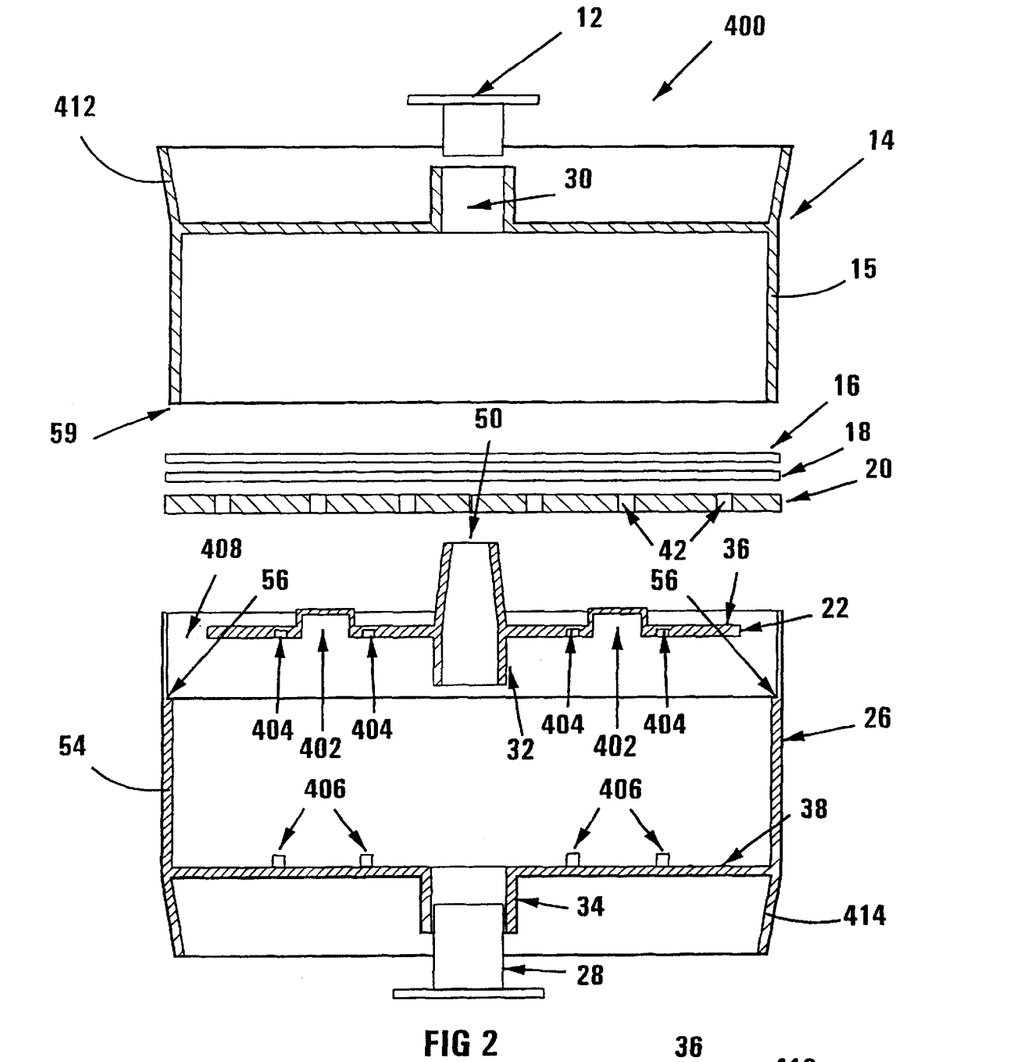
FIG. 2 is an exploded, sectioned side view of another embodiment of the culture monitor in accordance with the invention.

Referring to FIG. 2 of the drawings, reference numeral 400 generally indicates another embodiment of a culture monitor forming part of a device in accordance with the invention for microbiological testing of a liquid sample. Unless otherwise indicated, the same reference numerals used above with reference to FIG. 1, are used to indicate the same or similar parts or features.

Although, unlike the culture monitor 10, the wall of the first housing section 14 of the culture monitor 400 is not stepped, the major differences between the culture monitor 400 and the culture monitor 10 lie in the appearance of the second housing section 22.

The floor 36 of the second housing section 22 is shaped to define an annular compartment or channel 402. Two annular sealing channels 404 are also provided in an underside of the floor 36. The sealing channels 404 and the compartment or channel 402 are concentric. Two annular projections 406 are provided on the floor 38 of the third housing section 26. The projections 406 are in register with the sealing channels 404, and when the culture monitor 400 is assembled, the projections 406 fit male-female fashion in fluid-tight manner into the sealing channels 404. A dehydrated culture medium (not shown) is contained in the compartment or channel 402 when the culture monitor 400 is assembled.

The floor 36 of the second housing section 22 has a smaller diameter than the floor 38 of the third housing section 26. A flow path 408 is thus defined between the floor 36 and the wall 54. The support 20, the absorbent pad 18 and the filter medium 16 rest on the ledge or shelf 56 of the third housing section 26. In another embodiment (not shown) the absorbent pad 18 and support 20 have the same diameter as an inside diameter of the wall 54 and are supported below the shelf 56 such that an upper surface of the absorbent pad 18 is flush with the shelf 56. The filter medium 16 is thus seated directly on the shelf 56 and is sandwiched or clamped between the lower rim 59 of the first housing section 14 and the shelf 56 of the third housing section 26 in the same manner as shown in FIG. 1 of the drawings.

The first housing section 14 and the third housing section 26 each has a frustoconical body section 412 and 414 respectively. The body section 412 is shaped and dimensioned to receive the body section 414 of a similar culture monitor 400, thus rendering the culture monitor 400 stackable.

The culture monitor 400 is used in similar fashion as the culture monitor 10, as described above. However, when the long stemmed plug 28 is inserted into the lower outlet section 34, it prods against the upper outlet section 32 and further insertion of the long stemmed plug 28 forces the floor 36 of the second housing section 22 away from the floor 38 of the third housing section 26, thus breaking the seal formed between the projections 406 and the sealing channels 404, releasing the dry culture medium from the compartment or channel 402. At the same time, the filtrate retained in the culture monitor 400 a result of the raised inlet end 50 flows through the flow path 408 downwards and mixes with the dehydrated culture medium to rehydrate the culture medium. When the culture monitor 400 is then inverted, the rehydrated culture medium flows back through the flow path 408 to saturate the absorbent pad 18.

Figure 3:
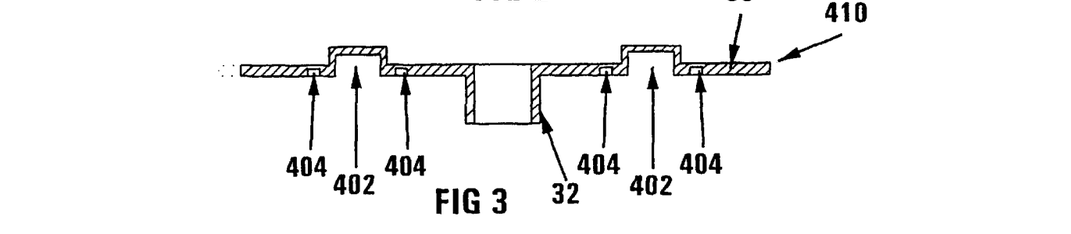
FIG. 3 is a sectioned side view of another embodiment of a second housing section for the culture monitor of FIG. 2.

Referring to FIG. 3 of the drawings, reference numeral 410 generally indicates another embodiment of a second housing section for the culture monitor 400 and unless Aim otherwise indicated, the same reference numerals used above with reference to the second housing section 22, are used to indicate the same or similar parts or features.

Unlike the second housing section 22, the second housing section 410 does not have a raised inlet end 50. Thus, in use, no filtrate is retained in the culture monitor 400 when the second housing section 410 forms part of the culture monitor 400. Instead, the compartment or channel 402 contains deionised, sterilized water, which is released from the compartment 402 in the same fashion as the dehydrated culture medium described above. The dehydrated culture medium in this case is contained in a slow-release capsule (not shown) which is located on the floor 36 of the second housing section 410. When the culture monitor 400 is inverted, the sterilized, deionised water flows through the flow path 408 to wet the capsule, typically dissolving the capsule in about 5–20 minutes, whereafter the water rehydrates the dehydrated culture medium contained in the capsule.

It is an advantage of the culture monitor 10, 400, 500 as illustrated, that it is not necessary to inject a culture medium broth into the culture monitor 10, 400, 500 which avoids the problem of a bulging filter medium 16 which may occur with conventional culture monitors. It is also an advantage of the culture monitor 10, 400, 500 as illustrated, that it contains sufficient rehydrated culture medium after rehydration to prevent the absorbent pad 18 from drying out. The applicant also believes that the device and method of the invention, as illustrated, provides for a simplified technique to conduct a microbiological test on a liquid sample, since it eliminates liquid culture medium handling and storage at low temperatures, and thus allows for a lower level of skill required by a user of the device of the invention, compared to conventional devices and methods. The dehydrated culture medium used with the device and method of the invention, typically has a shelf life of up to 5 years,- compared to a shelf life of about 12 months for pre-sterilized prior art ampoules of hydrated culture medium, which must be stored at low temperatures, typically 2–80C.

The applicant believes that filtrate from the liquid sample is a suitable rehydration agent for the dehydrated culture medium, since, if the liquid sample supported the growth of the target organism, then the sample filtrate will be equally suitable to be used as the rehydration agent.

What is claimed is:

1. A culture monitor for microbiological testing of a liquid sample, the culture monitor including
   a housing having a liquid inlet and a liquid outlet;
   liquid sample filtration means inside the housing between the liquid inlet and the liquid outlet, the liquid sample filtration means including a filter medium so that a liquid sample entering the housing through the liquid inlet passes through the filter medium, with microorganisms present in the liquid sample being retained on the filter medium and spent liquid or filtrate passing through the filter medium;

a dehydrated culture medium located between the filtration means and the liquid outlet; and a reservoir in the housing downstream of the liquid sample filtration means relative to the liquid inlet, with a volume of a rehydration agent for the dehydrated culture medium being provided in the reservoir or the reservoir being adapted to retain during filtration, as a rehydration agent, a portion of the filtrate, the dehydrated culture medium being located such that it is sealed or separated from the spent liquid or filtrate during filtration at least until immediately after filtration of a liquid sample and such that it can be brought into contact with the rehydration agent, after filtration, to form a rehydrated culture medium for the microorganisms retained on the filter medium.

2. A culture monitor as claimed in claim 1, in which the dehydrated culture medium is contained in a slow-release capsule of a cold water soluble material, the capsule thus sealing or separating the dehydrated culture medium from the spent liquid or filtrate during filtration of a liquid sample, at least until immediately after filtration of the liquid sample.

3. A culture monitor as claimed in claim 1, in which the reservoir is defined by a first chamber of the housing, the housing including a second chamber downstream of the first chamber relative to the liquid inlet, the liquid outlet extending through the second chamber, the first chamber and the second chamber being sealed from each other at least until immediately after filtration of a liquid sample, and the dehydrated culture medium being located in the second chamber.

4. A culture monitor as claimed in claim 3, in which a floor of the first chamber has a zone of weakness surrounding an inlet end of the liquid outlet such that exertion of a force on the liquid outlet effects failure of the zone of weakness, thereby to establish contact between the dehydrated culture medium and the rehydration agent.

5. A culture monitor as claimed in claim 3, in which the second chamber and the first chamber are each defined by a housing section, the housing sections being screw-threadedly attached or attachable to each other, with a sealed flow passage being provided between the chambers, the seal of the flow passage being configured to be pierced or broken when the chambers are advanced towards each other by rotating their housing sections relative to each other, thus, establishing flow communication between the two chambers.

6. A culture monitor as claimed in claim 3, in which the second chamber includes at least one compartment sealed or sealable from the rest of the second chamber, the compartment being configured to release its contents when so required.

7. A culture monitor as claimed in claim 6, in which the compartment is in the form of an annular channel formed between a floor of the first chamber and a floor of the second chamber, with the channel being sealed from the rest of the second chamber by complementary annular male and female formations on the floors of the chambers, and in which the dehydrated culture medium is located in the compartment in the second chamber.

8. A culture monitor as claimed in claim 1, in which the dehydrated culture medium is contained in a fragile or breakable capsule and is located in the housing such that it can be broken or crushed to release its contents.

9. A culture monitor as claimed in claim 1, in which the reservoir includes at least one compartment sealed or sealable from the rest of the reservoir, the compartment being configured to release its contents when so required, and in which the dehydrated culture medium is located in the compartment.

10. A culture monitor as claimed in claim 9, in which the compartment contains the rehydration agent.

11. A culture monitor as claimed in claim 1, in which the housing is adapted to allow the insertion of the dehydrated culture medium into the housing, between the filtration means and the liquid outlet, and which includes a cold water soluble gelling agent in the housing between the filtration means and the liquid outlet such that the gelling agent can be brought into contact with the rehydration agent and the dehydrated culture medium.

12. A culture monitor as claimed in claim 1, in which the liquid outlet of the housing is configured to allow only an excess portion of the filtrate to drain from the reservoir and to retain during filtration, as the rehydration agent, a portion of the filtrate.

13. A culture monitor as claimed in claim 12, in which an inlet end of the liquid outlet is raised above a floor of the reservoir, thereby to retain during filtration, as the rehydration agent, a portion of the filtrate.

14. A culture monitor as claimed in claim 1, in which the housing is modular, comprising at least two separable housing sections.

15. A culture monitor as claimed in claim 1, in which the liquid outlet is a two part outlet, comprising an upper section and a lower section, the two sections being displaceable relative to each other, and which includes interchangeable removable closure members for the liquid inlet and the liquid outlet, the closure members being in the form of plugs having elongate plug stems which fit spigot-socket fashion into the liquid inlet and outlet, one of the plugs having a longer plug stem than the other plug.

16. A culture monitor as claimed in claim 1, which includes pH indicating means inside the housing, downstream of the filtration means relative to the liquid inlet, and a non-target bacterial growth inhibitor inside the housing.

17. A culture monitor as claimed in claim 1, in which the filter medium is a membrane filter, the membrane filter being supported on an absorbent body, and which includes a hygroscopic substance inside the housing to control the humidity inside the housing.

18. A culture monitor as claimed in claim 1, which includes dissolution promoting means to promote the dissolution of the dehydrated culture medium when it is being rehydrated.

19. A kit for microbiological testing of a liquid sample, the kit including a culture monitor as claimed in claim 1; and a sample container for use with the culture monitor.

20. A kit as claimed in claim 19, in which the sample container includes a hollow body having a liquid outlet at a low elevation, the liquid outlet being connectable to the liquid inlet of the culture monitor, and which includes a base which is configured to support the culture monitor, the base including a suction or vacuum conduit which is connectable to the liquid outlet of the culture monitor.

21. A method of microbiologically testing a liquid sample, the method including
- filtering a liquid sample through a filter medium to retain microorganisms present in the liquid sample on the filter medium, with a filtrate passing through the filter medium;
- after filtration of the liquid sample, bringing a dehydrated culture medium into contact with a portion of the filtrate to provide a rehydrated culture medium; and
- contacting the rehydrated culture medium with the microorganisms on the filter medium thereby to culture the microorganisms.

22. A method as claimed in claim 21 which includes admixing a gelling agent with the rehydrated culture medium, thereby assisting in contacting the rehydrated culture medium with the microorganisms on the filter medium.

* * * * *